(12) United States Patent
Wang et al.

(10) Patent No.: US 8,735,591 B2
(45) Date of Patent: May 27, 2014

(54) ORGANIC AMINE DIMMER AND METHOD FOR SYNTHESIZING THE SAME

(75) Inventors: Sue-Lein Wang, Hsinchu (TW); Yu-Chuan Chang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 13/615,015

(22) Filed: Sep. 13, 2012

(65) Prior Publication Data
US 2013/0310566 A1 Nov. 21, 2013

(30) Foreign Application Priority Data

May 15, 2012 (TW) .............................. 101117207 A

(51) Int. Cl.
*C07D 401/14* (2006.01)
(52) U.S. Cl.
USPC ........................................................ 546/255
(58) Field of Classification Search
None
See application file for complete search history.

(56) References Cited

PUBLICATIONS

Zhang et al., In Situ Synthesis of Tetradentate Dye for Construction of Three-Dimensional Homochiral Phosphor, 20(17) Chem. Materials 5457-5459 (2008).*
Meng et al., Controllable self-assembly of two novel metal-organic frameworks based on different tetradentate in situ ligands, 13(2) Cryst. Eng. Commun. 649-655 (2011).*
Chang & Want, From Stimuli-Responsive Polymorphic Organic Dye Crystals to Photoluminescent Cationic Open-Framework Metal Phosphate, 134(24) J. Am. Chem. Soc. 9848-9851 (2012).*
Chang et al., "From Stimuli-Responsive Polymorphic Organic Dye Crystals to Photoluminescent Cationic Open-Framework Metal Phosphate," J. of the Amer. Chem. Soc., vol. 134, pp. 9848-9851 (2012).

* cited by examiner

*Primary Examiner* — Janet L Andres
*Assistant Examiner* — Timothy R Rozof
(74) *Attorney, Agent, or Firm* — Muncy, Geissler, Olds & Lowe, P.C.

(57) ABSTRACT

An organic amine dimmer and a method for synthesizing the same are disclosed. The method comprises the following steps: (A) mixing an iron-containing compound (e.g., $Fe_2O_3$, $FeCl_3$), a nitrate-containing compound, oxalate acid, 4,4'-trimethylenedipiperidine (TMDP), $H_3PO_4$, and 2 to 8 ml of water to form a mixture; (B) heating the mixture and maintaining the mixture at 160° C. or above for a first predetermined time; (C) cooling the mixture; and (D) placing the mixture at room temperature for a second predetermined time, to obtain an organic amine dimmer, wherein $Fe(NO_3)_3$ can serve as the iron-containing compound as well as the nitrate-containing compound.

7 Claims, 5 Drawing Sheets
(1 of 5 Drawing Sheet(s) Filed in Color)

ORGANIC AMINE DIMMER AND METHOD FOR SYNTHESIZING THE SAME

BACKGROUND OF THE INVENTION

1. Field of the Invention

The present invention relates to an organic amine dimmer and a method for synthesizing the same, and particularly to an organic amine dimmer having a molecular formula $C_{26}N_4H_{18}$ and a method for synthesizing the same.

2. Description of Related Art

Synthesis for novel fluorescent materials having a novel structure from 4,4'-trimethylenedipyridine (TMDP) have been increasing in recent years, wherein the synthetic processes comprise use of hydrothermal synthesis or solvent-thermal synthesis. In addition, some studies indicate that in-situ metal/ligand reaction may occur during TMDP synthetic process, which involves breakage of S—S bond in a disulfide compound, cycloaddition of a nitrile compound, hydroxylation and dehydrogenation polymerization of an aromatic ring, to form a metal coordination compound consisting of a metal and its ligand, such as 1,4-dihydroxy-1,2,4,5-tetra-(4-pyridyl)cyclohexane (CHTPY) or 1,2,4,5-tetra(4-pyridyl)benzene (TPB). Furthermore, to isolate the ligand from the compound, an acidic aqueous solution is needed to remove the metal, followed by recrystallization to form a ligand with hydration water.

In the existing organic synthesis, formation of a C—C bond usually employs a highly reactive and expensive organometallic agent for catalysis. The first method ever recorded in history for synthesizing a TMDP dimmer is carried out by catalyzing the reaction with $PdCl_2(PPh_3)_2$/LiCl and performing cross coupling to form the TMDP dimmer. However, forming a C—C bond by hydrothermal synthesis is not common.

Therefore, what is needed in the art is a method for directly synthesizing an organic amine dimmer in one-step without using expensive catalytic metal, and the synthesized organic amine dimmer has a high quantum efficiency to serve as a reflective material, a fluorescent material, or so forth.

SUMMARY OF THE INVENTION

An object of the present invention is to provide an organic amine dimmer which may serve as an effective reflective material or a fluorescent material.

Another object of the present invention is to provide a method for directly and quickly synthesizing a photoluminescent organic amine dimmer in one-step.

To achieve the objects, the present invention provides an organic amine dimmer having a molecular formula C26N4H18, wherein the crystal system of the organic amine dimmer is not particularly limited, and is preferably a monoclinic crystal system. The space group of the organic amine dimmer is also not particularly limited, and is preferably $P2_1/c$.

In addition, the organic amine dimmer has a lattice constant a of 5.96-5.98 Å, a lattice constant b of 11.41-11.43 Å, a lattice constant c of 13.98-14.00 Å, and a lattice constant β of 90.30-90.32°, and more preferably, the lattice constant a is 5.97 Å, the lattice constant b is 11.42 Å, the lattice constant c is 13.99 Å, and the lattice constant β is 90.31°

The organic amine dimmer of the present invention may be 1,2,4,5-tetra(4-pyridyl)benzene (TPB), having a chemical formula as formula I, which is free from hydration water.

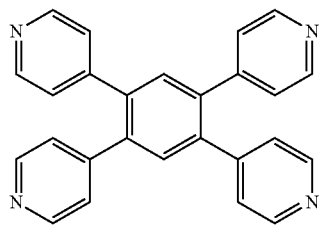

[formula 1]

Here, TPB is photoluminescent, and has a maximum excitation wavelength of 400-460 nm, and a maximum emission wavelength of 480-540 nm, but is not limited hereto. Alternatively, 1,2,4,5-tetra(4-pyridyl)benzene (TPB) has a maximum excitation wavelength of 270-300 nm, and a maximum emission wavelength of 325-385 nm. Preferably, TPB has a maximum excitation wavelength of 300 nm, and a maximum emission wavelength of 355 nm.

By the high quantum efficiency of 35-40% of the organic amine dimmer, the organic amine dimmer of the present invention may serves as an effective reflective material or a fluorescent material, and be widely used in DNA diagnosis, optical electronics, dyes, photochemical sensors, fluorescent coating paints, fluorescent brighteners, organic light-emitting diode (OLED), laser dyes, and so forth.

The present invention also provides a method for synthesizing an organic amines, which comprises the following steps: (A) mixing an iron-containing compound, a nitrate-containing compound, oxalate acid, 4,4'-trimethylenedipiperidine (TMDP), $H_3PO_4$, and 2 to 8 ml of water to form a mixture; (B) heating the mixture and maintaining the mixture at 160° C. or above for a first predetermined time; (C) cooling the mixture; and (D) placing the mixture at room temperature for a second predetermined time, to obtain an organic amine dimmer.

In the step (A) of the present invention, the iron-containing compound is not particularly limited, and may be $Fe_2O_3$, or $FeCl_3$. Besides, the iron-containing compound and the nitrate-containing compound may be a single compound including both iron and nitrate, such as $Fe(NO_3)_3$.

In the step (B) of the present invention, the way and the rate of heating the mixture is not particularly limited, and the heating rate is preferably 55-65° C./hr, and more preferably 60° C./hr. In addition, the temperature then maintains at above 160° C., and preferably 170-190° C., for a first predetermined time. However, the temperature and the first predetermined time are not limited, as long as the first predetermined time is sufficient for completing the hydrothermal reaction, which is preferably 1-2 days.

In the step (C) of the present invention, the mixture is preferably cooled with a rate of 2-10° C./hr, and more preferably 6° C./hr, though not particularly limited.

Furthermore, in the step (D) of the present invention, the second predetermined time is not particularly limited, and preferably 1-3 days, as long as the desirable compound can be crystallized at room temperature.

By the method for synthesizing an organic amine dimmer of the present invention, 1,2,4,5-tetra(4-pyridyl)benzene (TPB) can be directly synthesized in one-step without using expensive catalytic metal, and the synthesized organic amine dimmer has a high quantum efficiency to serve as a reflective material, a fluorescent material, or so forth.

The present invention performs a hydrothermal reaction using TMDP with addition of ferric nitrate, oxalate acid and phosphoric acid, to synthesize an anhydrous TPB in absence of metal coordination, and therefore, there is no need for steps of removing metal ions and recrystallization as required in the prior art. Furthermore, by adding phosphoric acid and controlling the amount of water addition, the synthesized compound may proceed with in-situ reaction without metal coordination, and thus a pure TPB with photoluminescent properties can be synthesized in one-step directly without using expensive catalytic metal. Therefore, the processing time and cost are greatly reduced.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT

In the following description, numerous specific details are set forth to provide a thorough understanding of embodiments of the present disclosure. However, one having an ordinary skill in the art will recognize that embodiments of the disclosure can be practiced without these specific details. In some instances, well-known structures and processes are not described in detail to avoid unnecessarily obscuring embodiments of the present disclosure.

EXAMPLE 1

TPB Synthesis

First, 0.4 mmol of $Fe(NO_3)_3$, 1.2 mmol of oxalate acid, 6.4 mmol of TMDP, 9 mmol of H3PO4, and 2 mL of deionized water were mixed to form a mixture.

Next, the mixture was placed in a teflon cup, heated with a rate of 60° C./hr, and then maintained at a temperature of 180° C. for 1-2 days. Thereafter, the mixture was by cooled with a rate of 6° C./hr.

Finally, the mixture was kept at room temperature for 1 day or more, to form anhydrous TPB and dihydrate TPB simultaneously.

Figure 1:
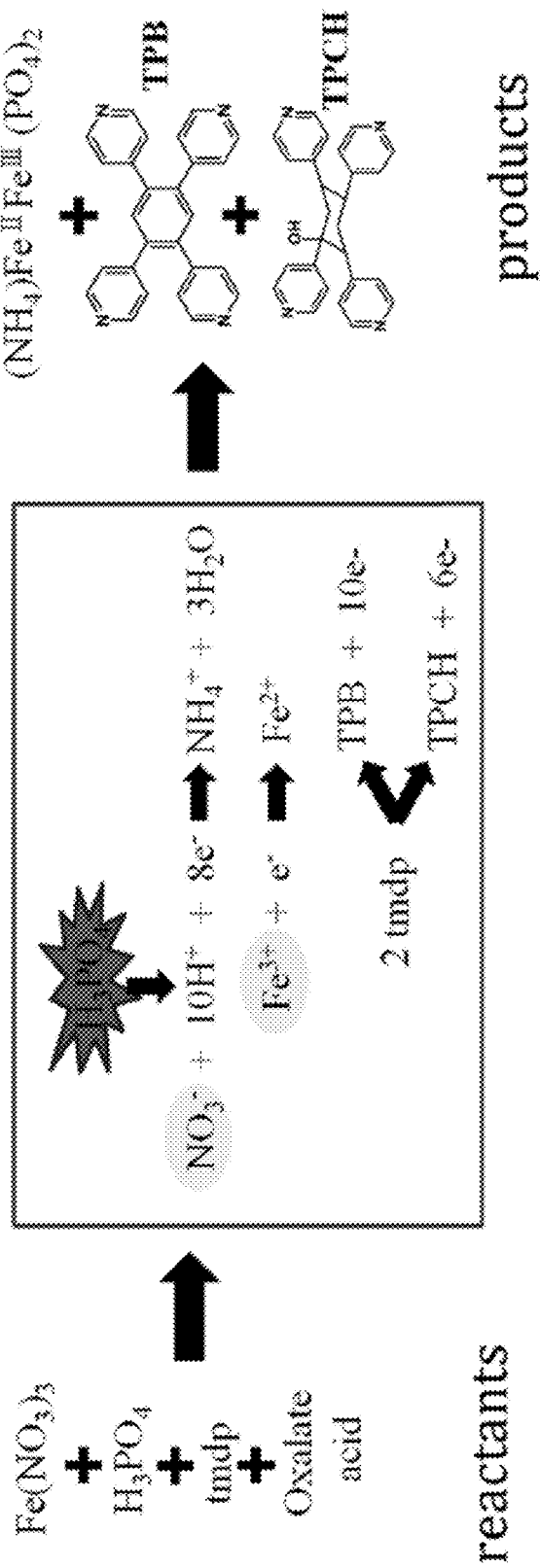
FIG. 1 shows the flow chart of the synthesis reaction according to Example 1 of the present invention.

FIG. 1 shows the flow chart of the synthesis reaction, wherein the left diagram illustrates the reactants, the middle diagram illustrates the reaction process, and the right diagram illustrates the products. In the reaction, $NO_3^-$ and $Fe_3^+$ served as the oxidants (marked by circle), wherein $NO_3^-$ was especially the major oxidant. Since many protons were needed for reducing $NO_3^-$ to $NH_4^+$, phosphoric acid added in the reaction served as a driving factor (marked by explosive circle). In the absence of phosphoric acid, the oxidizing power would be not enough, and only 1-hydroxy-1,2,4,5-tetra-(4-pyridyl)cyclohexane (TPCH) molecule can be obtained. In addition, the byproduct $(NH_4)Fe_2(PO_4)_2$ may be regarded as a strong evidence for this reaction mechanism due to the presence of $NH_4^+$ and divalent iron (ferrous ion) in the structure. Such a synthesis reaction involves a lot of electron migrations, and the OH group in TPCH may come from water in the reaction. A TPCH molecule was synthesized with release of six electrons, while a TPB molecule was synthesized with release of ten electrons.

<Characterization>

1. Crystal Property

In this example, the single-crystal diffractometer (Bruker APEX DUO) was used to identify the structure. Anhydrous TPB was named TPB-1, and dihydrate TPB was named TPB-2.

TABLE 1

| Compound | Crystal system/ space group | Lattice constant (Å), (deg) | Volume (Å3)/ Z/D(g/cm3)/Fw |
|---|---|---|---|
| $C_{26}N_4H_{18}$ (TPB-1) | Monoclinic crystal/P2₁/c | a = 5.9714(4) Å<br>b = 11.4212(8) Å<br>c = 13.996(2) Å<br>β = 90.312° | V = 954.5(1)<br>Z = 2<br>D = 1.345<br>Fw = 386.44 |
| $C_{26}N_4H_{18} \cdot 2H_2O$ (TPB-2) | Monoclinic crystal/C2/c | a = 16.310(2) Å<br>b = 13.683(2) Å<br>c = 9.752(1) Å<br>β = 97.14(1)° | V = 2159.3(1)<br>Z = 4<br>D = 1.299<br>Fw = 422.48 |

2. Photoluminescence Property

Figure 2:
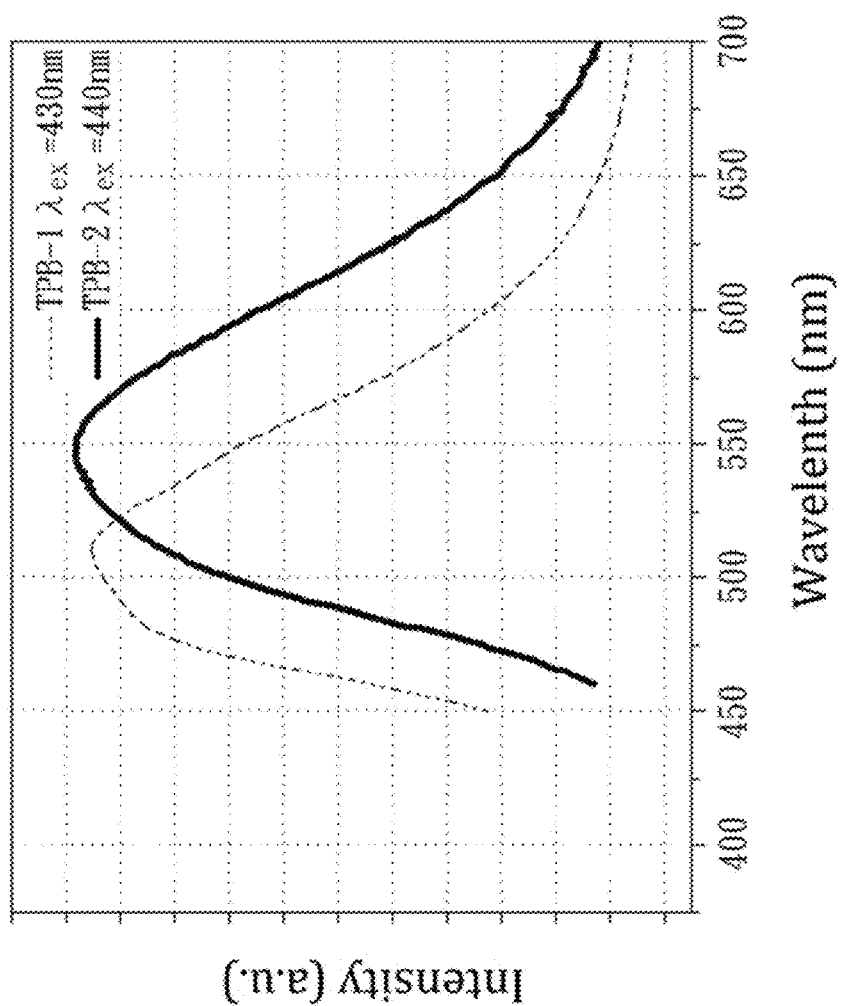
FIG. 2 shows the photoluminescence emitting spectrum of TPB-1 and TPB-2 according to the present invention.

The fluorescence spectrometer (HORIBA jobin yvon) was used to identify the photoluminescence properties. FIG. 2 shows the photoluminescence emitting spectrum, which indicates the emitting range. FIG. 2 and Table 2 show the photoluminescence properties of TPB-1 and TPB-2.

TABLE 2

| Compound | Maximum emission wavelength (λmax)(nm) | Maximum excitation wavelength (λmax)(nm) | CIE | Intermolecular π-π effect(Å) | Quantum yield (%) | Full width at half maximum (FWHM) (nm) |
|---|---|---|---|---|---|---|
| $C_{26}N_4H_{18}$ (TPB-1) | 510, 355 | 430, 300 | (0.22, 0.41) | 3.505, 3.612<br>3.702, 3.705 | 39.5 | 110 |
| $C_{26}N_4H_{18} \cdot 2H_2O$ (TPB-2) | 550, 370 | 440, 300 | (0.30, 0.48) | 3.589, 3.654 | 42.3 | 130 |

Figure 3A:
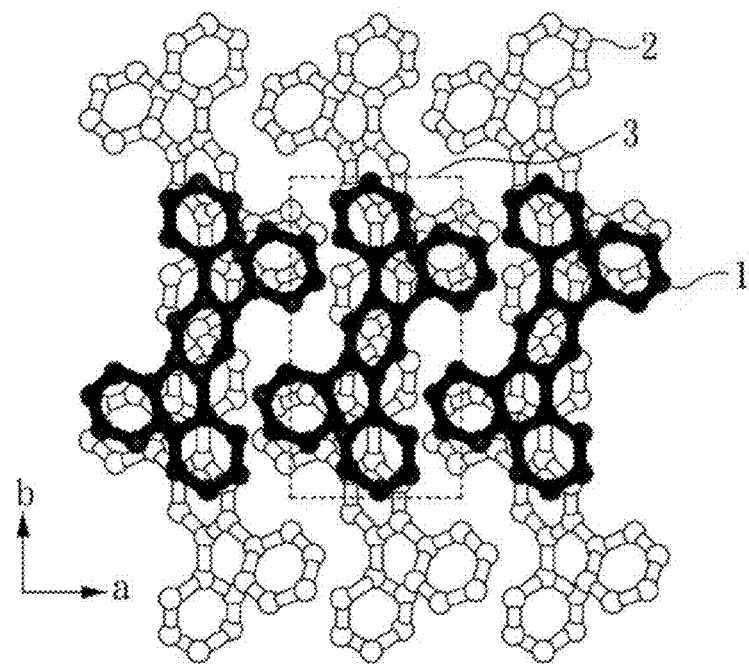
FIG. 3A shows the schematic view of the orientation structure of TPB-1 in a-axis direction according to the present invention.
Figure 3B:
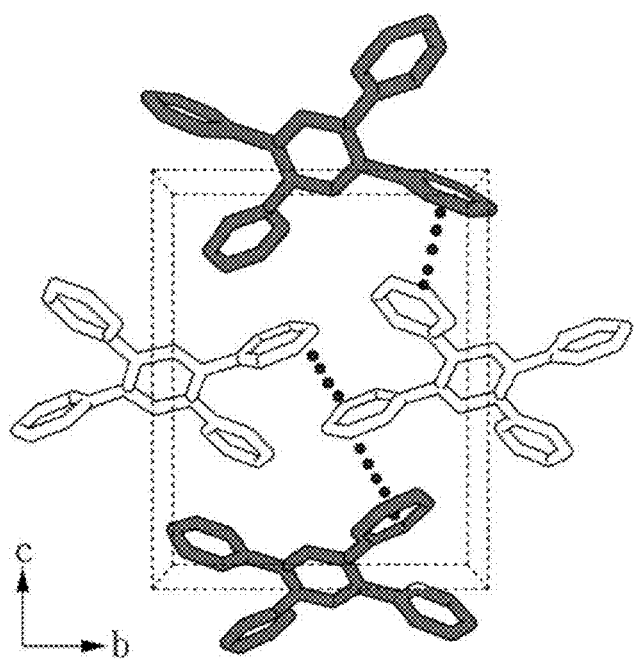
FIG. 3B shows the schematic view of the π-π interaction of TPB-1 according to the present invention.
Figure 4A:
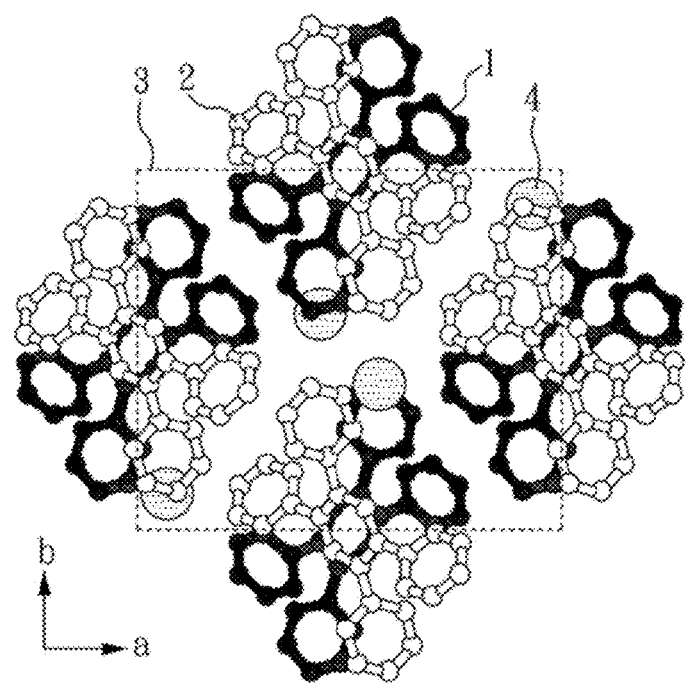
FIG. 4A shows the schematic view of the orientation structure of TPB-2 in a-axis direction according to the present invention.
Figure 4B:
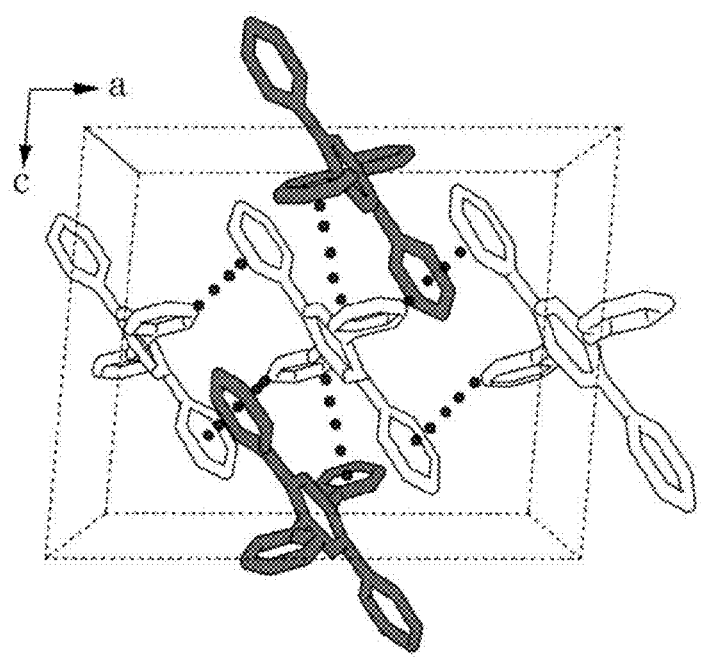
FIG. 4B shows the schematic view of the π-π interaction of TPB-2 according to the present invention.

FIGS. 3A and 3B show the schematic views of the orientation structure in a-axis direction and the π-π effect of TPB-1 respectively. In FIG. 3A, reference numeral 1 and 2 represent structures of Formula I in different levels respectively. In FIG. 3B, reference numeral 3 represents the π-π interaction area. That is, the area marked by reference numeral 3 in FIG. 3A is illustrated in FIG. 3B, and the area marked by reference numeral 3 in FIG. 4A is illustrated in FIG. 4B. Reference numeral 4 in FIG. 4 represents water molecule.

3. Stimuli-Responsive Property

Figure 5:
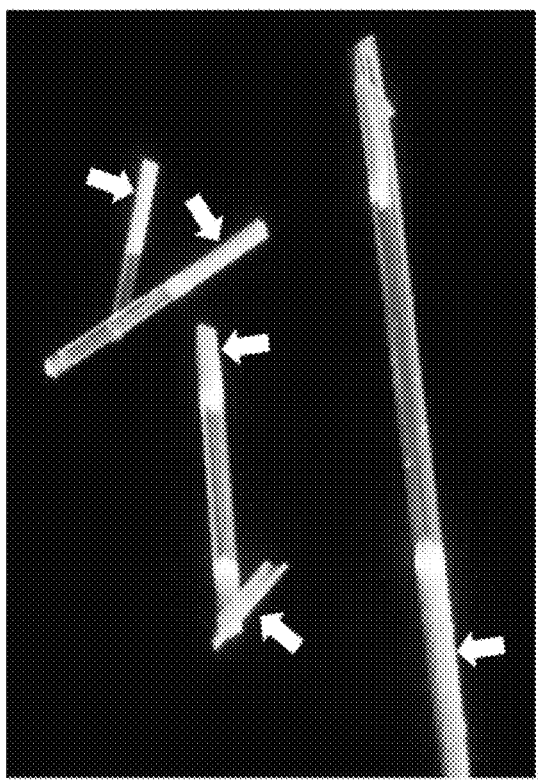
FIG. 5 shows the experiment result of the stimuli-responsive property according to the present invention.

FIG. 5 shows the crystal of TPB-2. When TPB-2 was optionally heated to a temperature of above 100° C., the molecular structure in the heated area (pointed by arrowhead) of TPB-2 may be rearranged into TPB-1 to show a white color. As such, two kinds of chromatic lights can be emitted from one crystal. Vice versa, TPB-1 may be recrystallized into TPB-2.

In the preceding detailed description, the present invention is described with reference to specifically exemplary embodiments thereof. It will, however, be evident that various modifications, structures, processes, and changes may be made thereto without departing from the broader spirit and scope of the present disclosure. The specification and drawings are, accordingly, to be regarded as illustrative and not restrictive. It is understood that embodiments of the present disclosure are capable of using various other combinations and environments and are capable of changes or modifications within the scope of the invention as expressed herein.

What is claimed is:

1. A method for synthesizing 1,2,4,5-tetra(4-pyridyl)benzene (TPB), comprising the following steps:
    (A) mixing an iron-containing compound, a nitrate-containing compound, oxalate acid, 4,4'-trimethylenedipiperidine (TMDP), $H_3PO_4$, and 2 to 8 mL of water to form a mixture;
    (B) heating the mixture and maintaining the mixture at 160° C. or above for a first predetermined time;
    (C) cooling the mixture; and
    (D) placing the mixture at room temperature for a second predetermined time, to obtain an organic amine dimmer;
    wherein the iron-containing compound is at least one iron-containing compound selected from a group consisting of $Fe_2O_3$, $FeCl_3$, and $Fe(NO_3)_3$.

2. The method for synthesizing 1,2,4,5-tetra(4-pyridyl)benzene (TPB) of claim 1, wherein in the step (A), the iron-containing compound and the nitrate-containing compound are both $Fe(NO_3)_3$.

3. The method for synthesizing 1,2,4,5-tetra(4-pyridyl)benzene (TPB) of claim 1, wherein in the step (B), the mixture is heated with a rate of 55-65° C./hr.

4. The method for synthesizing 1,2,4,5-tetra(4-pyridyl)benzene (TPB) of claim 1, wherein in the step (B), the mixture is heated and maintained at 170-190° C. for a first predetermined time.

5. The method for synthesizing 1,2,4,5-tetra(4-pyridyl)benzene (TPB) of claim 1, wherein in the step (B), the first predetermined time is 1-2 days.

6. The method for synthesizing 1,2,4,5-tetra(4-pyridyl)benzene (TPB) of claim 1, wherein in the step (C), the mixture is cooled with a rate of 2-10° C./hr.

7. The method for synthesizing 1,2,4,5-tetra(4-pyridyl)benzene (TPB) of claim 1, wherein in the step (D), the second predetermined time is 1-3 days.

* * * * *